United States Patent
Obradovic

(10) Patent No.: US 10,034,786 B2
(45) Date of Patent: Jul. 31, 2018

(54) MEDICAL IMPLANT

(71) Applicant: Bentley InnoMed GmbH, Hechingen (DE)

(72) Inventor: Milisav Obradovic, Lorrach (DE)

(73) Assignee: Bentley InnoMed GmbH, Hechingen (DE)

( * ) Notice: Subject to any disclaimer, the term of this patent is extended or adjusted under 35 U.S.C. 154(b) by 53 days.

(21) Appl. No.: 15/039,331

(22) PCT Filed: Nov. 28, 2014

(86) PCT No.: PCT/EP2014/075942
§ 371 (c)(1),
(2) Date: May 25, 2016

(87) PCT Pub. No.: WO2015/079023
PCT Pub. Date: Jun. 4, 2015

(65) Prior Publication Data
US 2017/0156898 A1 Jun. 8, 2017

(30) Foreign Application Priority Data
Nov. 28, 2013 (DE) .......................... 10 2013 019 890

(51) Int. Cl.
*A61F 2/90* (2013.01)
*A61F 2/844* (2013.01)
*A61F 2/848* (2013.01)

(52) U.S. Cl.
CPC ................ *A61F 2/90* (2013.01); *A61F 2/844* (2013.01); *A61F 2/848* (2013.01); *A61F 2002/8483* (2013.01); *A61F 2002/8486* (2013.01)

(58) Field of Classification Search
CPC .................................. A61F 2/07; A61B 17/12
(Continued)

(56) References Cited

U.S. PATENT DOCUMENTS

2003/0004541 A1* 1/2003 Linder ................... A61F 2/013
606/200
2004/0122467 A1 6/2004 Vantassel et al.
(Continued)

FOREIGN PATENT DOCUMENTS

CN 202143640 2/2012
EP 2338420 A1 6/2011

*Primary Examiner* — Suzette J Gherbi
(74) *Attorney, Agent, or Firm* — Berliner & Associates

(57) ABSTRACT

The invention relates to a medical implant (1) for the occlusion of a patients auricula sinistra by endovascular means, said implant having a cage structure (10) comprising a plurality of webs (3) that are proximally attached to a retaining ring (4) via connecting webs (2) and distally limited by a rim of converging webs (3), wherein said implant (1) consists of a self-expanding material, has in contracted state the shape of a slotted tube and, after expansion, assumes the cage structure (10) of a diameter larger than that of the retaining ring (4) and wherein at least one or several anchor elements (7) are arranged within or distally to the cage structure (10); said anchor elements being proximally connected directly or indirectly with the retaining ring (4), therein (a) the one or more anchor elements (7a) are provided at the distal end with a tip (8) with barb (9), with tip (8) and barb (9) projecting beyond the cage structure (10) with the intention for the tip (8) and barb (9) to be anchored in the muscle tissue of the auricula sinistra, or (b) the one or more anchor elements (7b) project laterally beyond the cage structure (10), extend in proximal direction in a curved configuration with the intention to be laterally supported against the muscle tissue of the auricula sinistra, or (c) a combination of alternatives (a) and (b) is provided.

18 Claims, 5 Drawing Sheets

Figure 3:
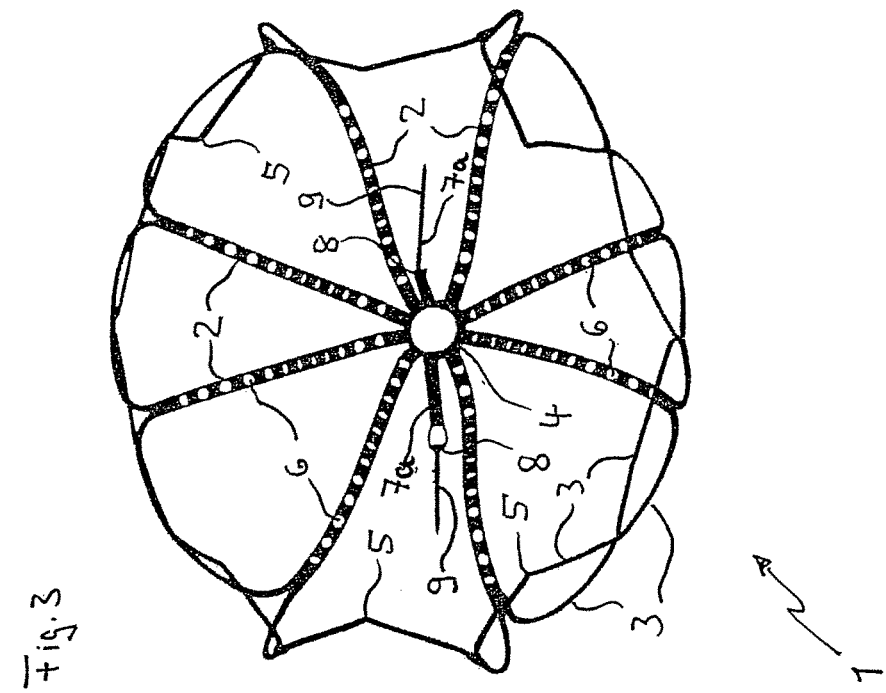

(58) Field of Classification Search
USPC .............................. 606/200; 623/1.35–1.48
See application file for complete search history.

(56) References Cited

U.S. PATENT DOCUMENTS

| | | | |
|---|---|---|---|
| 2005/0113933 A1* | 5/2005 | Carter | A61F 2/07 623/23.7 |
| 2011/0054515 A1* | 3/2011 | Bridgeman | A61B 17/0057 606/200 |
| 2012/0083823 A1* | 4/2012 | Shrivastava | A61F 2/01 606/200 |
| 2013/0245666 A1* | 9/2013 | Larsen | A61B 17/0057 606/198 |
| 2014/0336699 A1* | 11/2014 | van der Burg | A61B 17/0057 606/213 |
| 2015/0005810 A1* | 1/2015 | Center | A61F 2/01 606/200 |
| 2015/0133989 A1* | 5/2015 | Lubock | A61B 17/0057 606/200 |
| 2016/0278749 A1* | 9/2016 | Javois | A61B 17/12122 |
| 2017/0095256 A1* | 4/2017 | Lindgren | A61B 17/12122 |
| 2017/0156840 A1* | 6/2017 | Edmiston | A61F 2/01 |
| 2017/0215889 A1* | 8/2017 | Edmiston | A61B 17/12122 |
| 2017/0224354 A1* | 8/2017 | Tischler | A61B 17/12122 |

\* cited by examiner

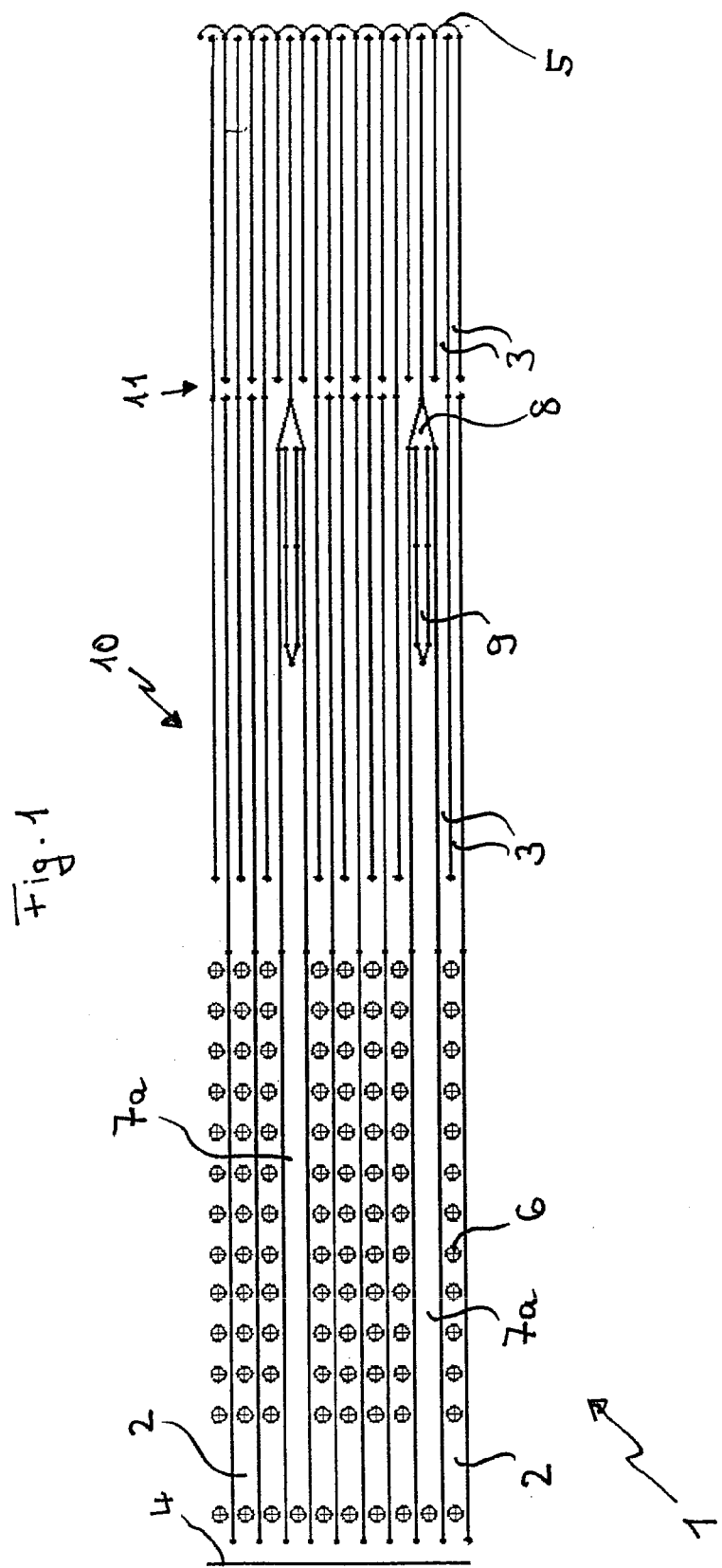

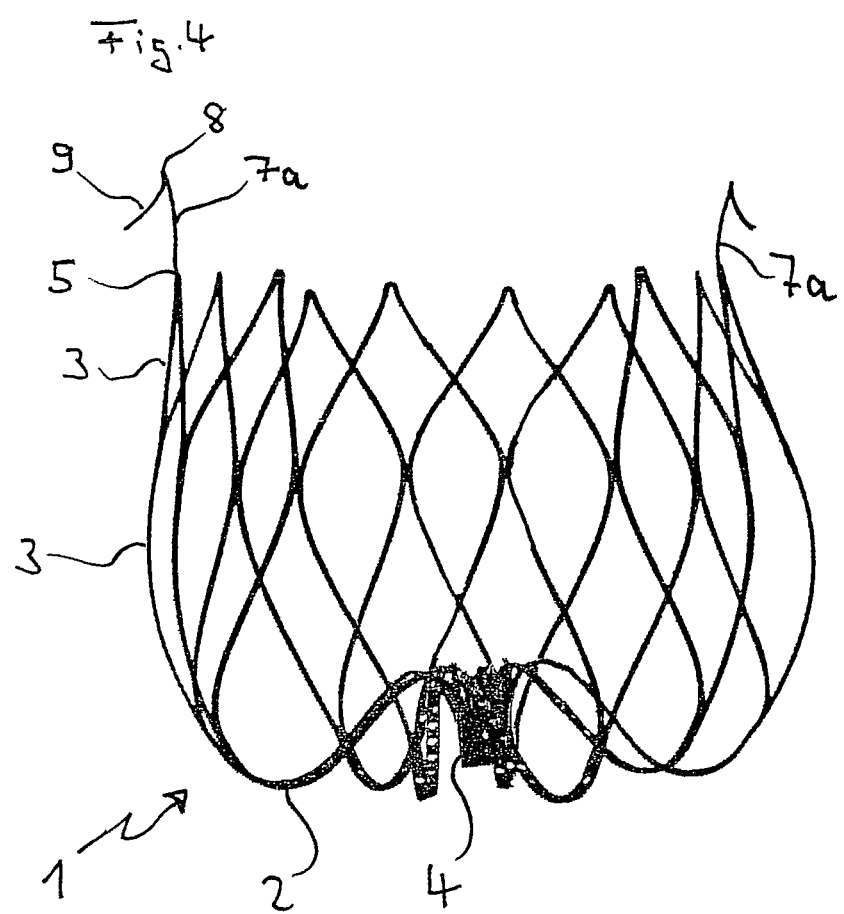

MEDICAL IMPLANT

The invention relates to a medical implant for the occlusion of a patient's auricula sinistra by endovascular means, said implant having a cage structure comprising a plurality of webs that are proximally attached to a retaining ring via connecting webs and distally limited by a rim of converging webs, with said implant consisting of a self-expanding material having in contracted state the shape of a slotted tube and, alter expansion, assuming a cage structure of a diameter larger than that of the retaining ring.

The auriculae atrii or auricles of atria are pouches of the atria of the heart in mammals. The left auricle of atrium, medically referred to as auricula sinistra, is situated beside the strand of the pulmonary artery and often the point of origin where blood clots form that may lead to apoplexy, especially with patients suffering from atrial fibrillation (AF). For that reason, ruling out the formation of dots in the auricula sinistra is an effective stroke prophylaxis for patients at risk.

Implants have been developed for this stroke prophylaxis that are placed info the pouches and occlude the access mostly by a braiding or a film. In Anglo-Saxon literature these implants are referred to as LAA occluders (LAA meaning left atrial appendage). These implants are placed into the pouches where they are anchored by means of bracing elements; they occlude the access with their proximal ends. The placement of the implants is usually effected via endovascular techniques, i.e. using a catheter, by means of which the implant is taken to the placement site in volume-reduced form, then released from the catheter and allowed to expand, implant expansion as a rule is brought about by self-expanding materials, for example shape-memory alloys.

Securing or anchoring the implants correctly and reliably is frequently a problem. Size and shape of the auricula sinistra may vary torn patient to patient and especially with regard to its access opening may be narrower or wider. Therefore, implants expanded and thus braced against the walls of the auricula may slip out of position and for that reason be unable to serve the intended purpose in the best possible way. In such cases it may still occur that thrombi are flushed out, in particular in physically stressed patients.

In view of the above, it is the objective of the present invention to propose an implant for the auricula sinistra that enables a reliable seat and an optimum shielding against the blood circulation system to be achieved.

This objective is reached with an implant of the kind first mentioned above that is provided with one or several anchoring elements proximally connected directly or indirectly with the retaining ring wherein
a) the one or more anchor elements are provided at the distal end with a barbed tip, with the tip and barb projecting beyond the cage structure with the intention for the barbed tip to be anchored in the muscle tissue of the auricula sinistra, or
b) the one or more anchor elements project laterally beyond the cage structures extend in proximal direction in a curved configuration with the intention to be late rally supported against the muscle tissue of the auricula sinistra, or
c) a combination of alternatives (a) and (b) is provided.

All alternatives (a) to (b) are suited to ensure the implant is reliably seated in the auricula sinistra due to the fact that the implant is secured and held in position in the auricula sinistra.

The inventive implant is provided with a retaining ring which is attached via a plurality of webs to the cage structure arranged distally to the retaining ring. In expanded stale of the implant the cage structure is much wider than the retaining ring. Said cage structure consists of a plurality of webs that expediently form a mesh or net structure. Whereas the cage structure at the proximal end is provided with the retaining ring it is open distally and terminates in a rim of zigzag-shaped and converging webs. The cage structure, in particular, consists of a meshwork of branching out and again converging webs.

For the purpose of being anchored in the muscle tissue of the auricula sinistra in accordance with alternative (a) the inventive implant is provided with one or several anchor elements protruding beyond the cage structure with each of these anchor elements terminating in a barbed tip intended to be hooked into the muscle tissue. For anchoring in the auricula sinistra as per alternative (b) the implant according to the invention has one or several anchor elements protruding laterally from the cage structure, being of curved configuration towards the proximal end and serving the purpose of laterally bracing the implant against the muscle tissue of the auricula sinistra. In this case the anchor elements form a second cage open towards the proximal end, wherein the ends of the anchor elements define the rim of the cage and brace themselves against the muscle tissue laterally to the entrance to the auricula sinistra. In this case as well the ends of the anchor elements may, if necessary, also have barbs but it will usually suffice for the ends to be rounded. In the latter case as well the bracing ensures the implant will be securely supported in the auricula sinistra.

The one or several anchor elements start directly or indirectly from the retaining ring and protrude beyond the cage structure so that they can make contact with the muscle tissue of the auricula sinistra in accordance with an embodiment of alternative (a) the one or more anchor elements are situated at the distal tips of the cage structure rim. The barbs may point to the outside or inside; preferably, the barbs are arranged on the outside. In the event several anchor elements are provided, these are preferably equally spaced over the rim, but not every tip of the rim must necessarily have an anchor element.

However, preferred is a variant as per alternative (a) providing for the anchor element breach anchor element to start from the retaining ring of the implant and extend through the cage structure and protrude distally beyond said structure. Accordingly, the one or several anchor elements are located approximately in the middle of the cage structure. Also in this case, a regular distribution of the anchor elements is preferred when several anchor elements are provided.

The medical implant proposed by the invention is transported to the placement site by means of a customary catheter from which it is released at placement site. Inside the catheter the implant is arranged in volume-reduced, contracted, and elongated form and essentially has the shape of a multi-slotted tube. The shape coincides with that of the tube from which the implant is produced by laser opting.

Having been released from the catheter the implant assumes the expanded form imprinted on it by a tempering method, i.e. it expands into the cage structure with anchor elements protruding beyond it.

For placement the implant transported inside the catheter is connected via the retaining ring and by means of a coupling mechanism with a guide element, preferably a guide catheter or guidewire. During placement, the implant is pushed into the auricula sinistra fey means of the guide element, following which its expansion is initiated. When the expansion is complete, the tips and barbs of the anchor elements situated in the center of the cage structure are heated outside of the cage. Using the guide catheter and/or guidewire the required pressure can be exerted as necessary to anchor the barbed tips in the muscle tissue of the rear wall of the auricula. The tips with barbs grow in without any problems and securely retain the implant in the selected position. After placement, the guide element is detached from the implant in a customary manner and withdrawn together with the catheter. Coupling mechanisms of this kind are known and have frequently been described in literature.

The cage structure of the inventive medical implant is normally attached to the retaining ring via 6 to 12 connecting webs. A number of 8 or 10 connecting webs have proven their worth, with said webs branching into the cage structure end distally converging to form the terminating rim.

Provided the webs are spaced sufficiently dense, the inventive implant may serve its purpose as thrombi filter without a covering or blanket needed. However, it is considered expedient for the medical implant to be provided with a covering in the proximal area, for example a polyurethane, polyester or Teflon film or coat. To enable such a covering to be attached to the cage structure it is moreover viewed expedient to provide perforations in the connecting webs extending from the retaining ring which can be used for sewing up the covering. However, the covering may also be attached by an adhesive method or by (repeated) immersion of the implant in a plastic solution or dispersion.

Preferably, the implants proposed by the invention are provided inside the cage with one or several anchor elements that extending from the retaining ring in alternative (a) protrude like lances from the opening of the cage structure and have a tip with at least one barb. Tip and barb are located outside of the cage structure and if adequate pressure is exerted during placement by means of the guide wire are capable of entering the muscle tissue of the auricula sinistra and securely hook themselves in place. As per alternative (b) the anchor elements protrude laterally beyond the cage structure and extend towards the proximal end in a curved configuration so that they brace the implant against the side wall in the entry region of the auricula sinistra. A combination of the two variants (a) and (b) can also be used. In this manner, the implant will be reliably secured such that the proximal part of the cage with the retaining ring is positioned in the entry region. The cage with or without covering will thus shield the auricula sinistra and prevent blood clots from being flushed out.

The same applies analogously to the arrangement of the anchor elements at the cage rim in which case the anchor elements form the distal end of the cage.

Basically, an anchor element as per alternative (a) will be sufficient; however, the implant is preferably provided with two or more anchor elements equally spaced over the circumference of the retaining ring. Especially preferred is an arrangement with two anchor elements oppositely located on the retaining ring.

The anchor elements in the center of the cage essentially extend in parallel roughly in the middle of the cage structure.

As per alternative (b) a plurality of anchor elements is considered advantageous, with the number of the elements depending on the number of the connecting webs between the retaining ring and the cage. In this case as well the anchor elements are equally spaced over the circumference of the retaining ring. Expediently, they are each arranged between two connecting webs.

As explained hereinbefore, the cage structure preferably is a meshwork of branching out and converging webs that form diamond-shaped structures. Due to the converging webs in the distal area a rim of converging webs of zigzag-shaped configuration is created the tips of which being preferably rounded. A meandering, curved shape or configuration may also be provided. When the anchor elements are arranged on the rim, a zigzag-shaped contour is preferred, with the anchor elements being attached to the tips of the rim.

At the proximal end of the cage structure the central retaining ring is preferably arranged within a central deepening portion of the cage structure. This means, the connecting webs between the retaining ring and the cage structure are S-shaped, i.e. extending from the distal side of the retaining ring they initially run in proximal direction before they again extend distally and merge into the cage structure.

As per another embodiment of the invention the anchor elements are arranged distally to the cage structure and extend laterally beyond the cage structure in this case, the anchor elements originate from a retaining tube that is attached to the retaining ring of the cage structure. Advantageously, the diameter of the retaining tubs is slightly smaller than that of the retaining ring, and said tube is fitted into and attached to said ring, for example by welding.

The anchor elements in this embodiment are preferably connected with each other in pairs at the tips so that they form into a kind of loop. The tips of this arrangement may be bent back into the cage so as to enable the anchor elements to brace themselves with their outer surfaces peripherally against the auricula sinistra.

The implants proposed by the invention consist of a flexible, self-expanding material. This material may be metal or plastic but expediently a metal alloy having shape-memory properties. Especially preferred are nickel-titanium alloys, for example Nitinol. How to manufacture implants consisting of these materials and their forming by tempering have frequently been described. When subjected to external force shape-memory metals of this kind are capable of assuming their originally manufactured form, and when such external force is omitted assume a shape again that has been later imprinted on it and fixed by tempering. This enables such implants to be transported in and by means of a catheter of small diameter and their subsequent expansion after they have been released from the catheter.

Accordingly, the inventive implants are manufactured from a tube by laser cutting after which a subsequent thermal forming method is applied to bring about their expanding shapes.

If made of a shape-memory alloy, the inventive implants may also consist of two parts cut out of separate tubes, in this way, one tube may be used to manufacture the cage whereas a second tube is employed for the anchor elements, with a retaining ring being provided in any case. The two parts are appropriately pined particularly by welding to form an implant.

The invention is explained in more detail by way of the enclosed figures, where

Figure 2:
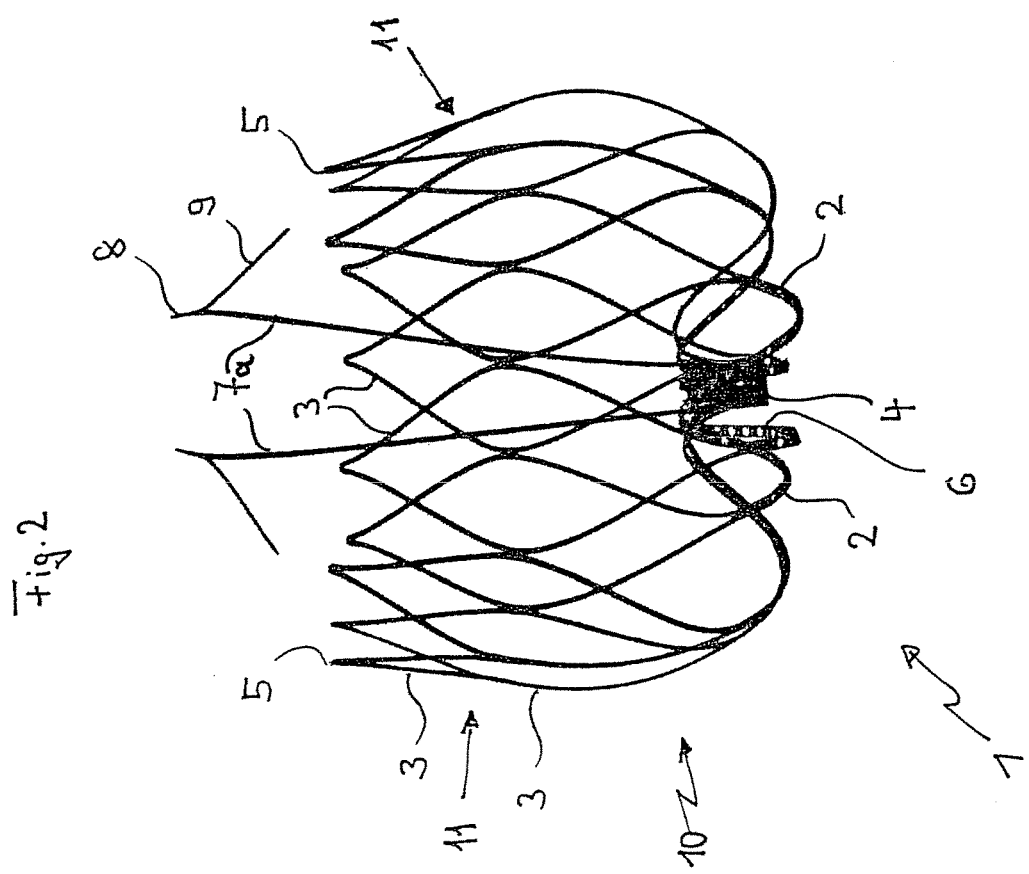
Figure 5:
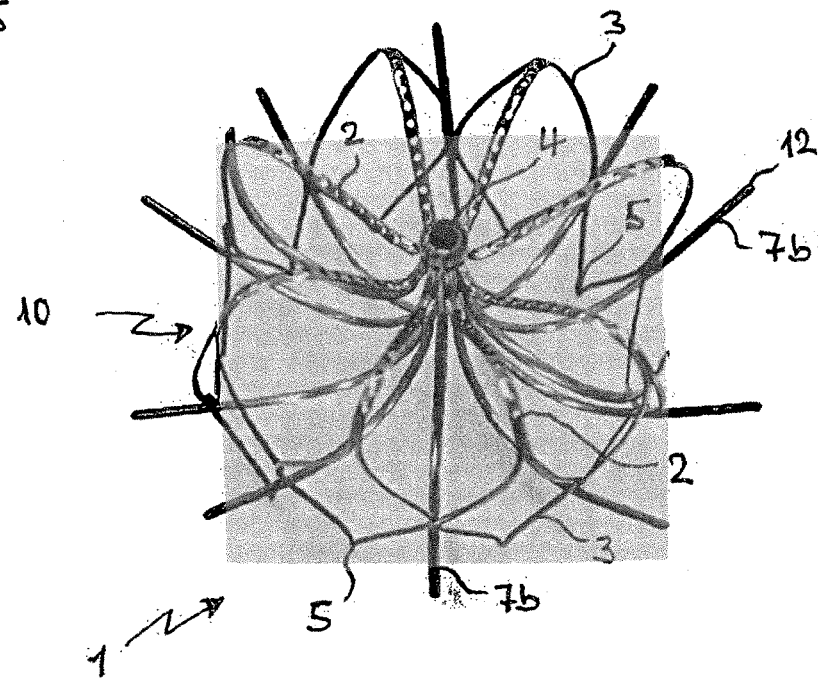
Figure 6:
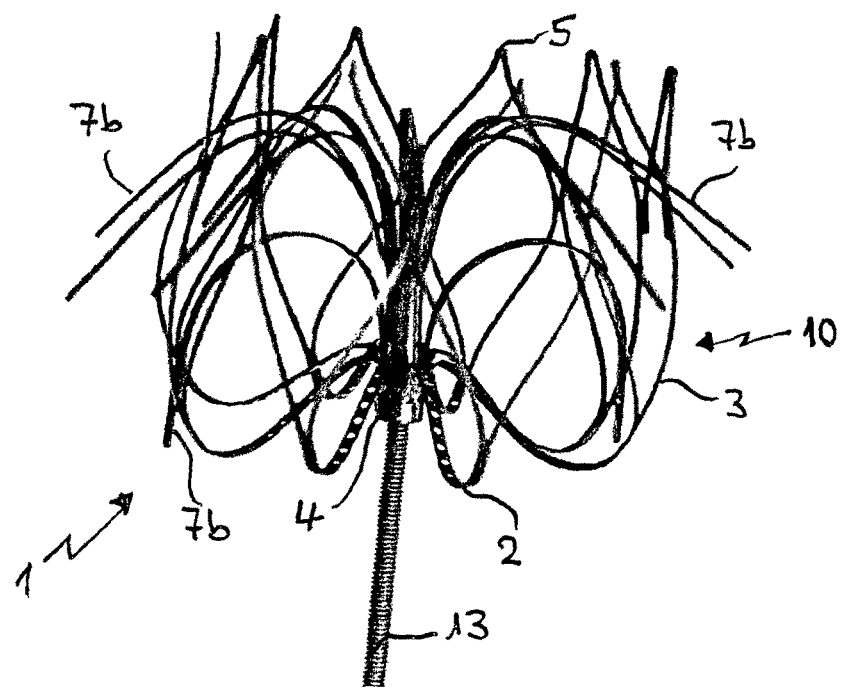
Figure 7:
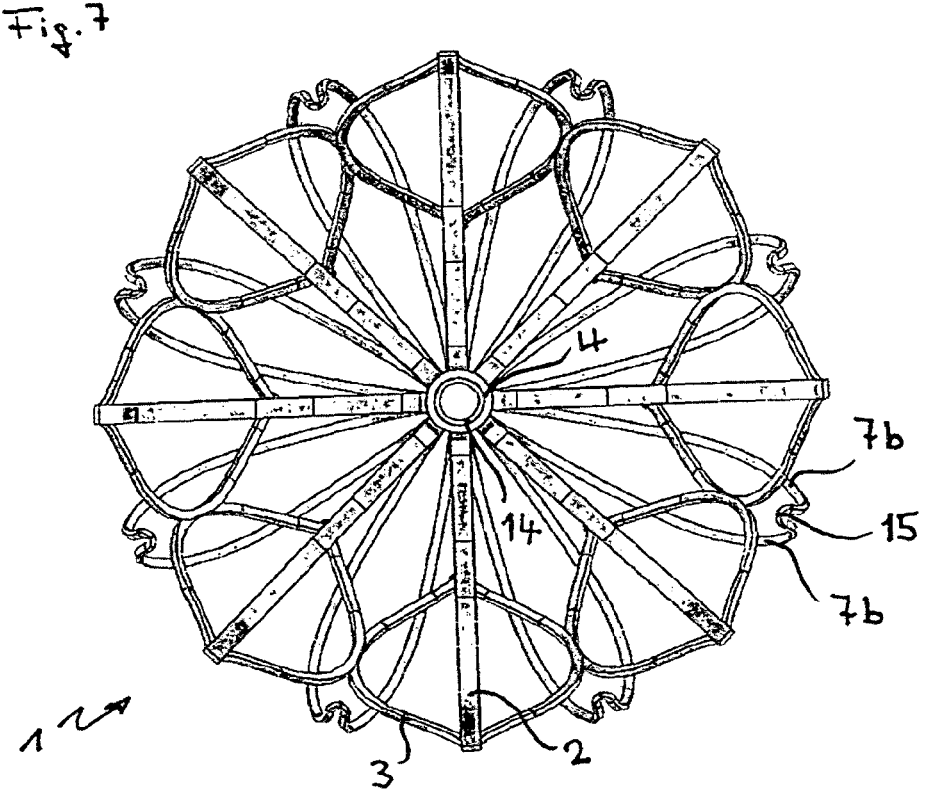
Figure 8:
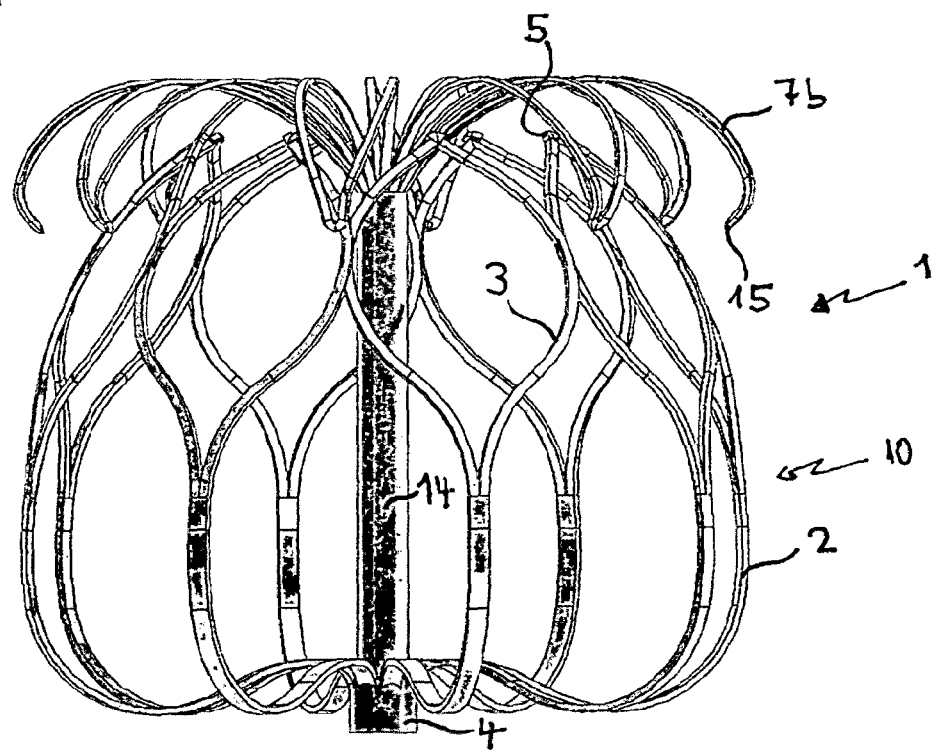

FIG. 1: is a planar view of a cutting pattern for an inventive implant in accordance with alternative (a);

FIG. 2: is a side view of an implant made of a tube according to FIG. 1;

FIG. 3: is a representation of the implant as per FIG. 2 seen from the proximal side;

FIG. 4: is a side view of another embodiment of an inventive implant in accordance with alternative (a);

FIG. 5: is a photographic representation of an embodiment of an inventive implant as per alternative (b);

FIG. 6: is another photograph of the implant as per FIG. 5 coupled to a guidewire;

FIG. 7: shows another embodiment of an inventive implant with anchor elements arranged distally to the cage structure; and FIG. 8: is a side view of the implant shown in FIG. 7.

FIG. 1 illustrates a planar representation of a cutting pattern for an inventive implant as per alternative (a), i.e. in cut-open and spread form prior to thermal forming. This representation thus shows the originally processed tube as a planar view.

From a retaining ring 4 a plurality of connecting webs 2 extend that each are provided with several perforations 8 serving to accommodate a covering, for example a Teflon film or coat attached by sewing. Each of the connecting webs 2 merge into two cage webs 3 which are linked with each other at intersection plane 11. In the distal region of the cage structure 10 two cage webs 3 each converge to form a rounded tip 5, with the total number of tips 5 forming the rim- or wreath-like boundary of cage 10.

Extending from the retaining ring 4 two anchor elements 7a are cut out that terminate in a tip 8. By making incisions a hook element 9 is defined which in reshaped form constitutes barb 9 of the tip 8.

FIG. 2 shows a photographic representation as side view of an inventive implant according to alternative (a) with retaining ring 4 and cage structure 10. A plurality of connecting webs 2 extend from the retaining ring and branch out to form the cage structure 10 with its cage webs 3. Cage webs 3 from which the connecting webs 2 extend converge in plane 11 where they branch out and finally converge again. At points of connection in the distal region of the cage, tips 5 are formed that preferably have a rounded contour.

Two lance-like anchor elements 7a extend from retaining ring 4, said elements are provided with barb 9 in the area of tips 8. These anchor elements protrude beyond the cage structure 10 and serve to secure the implant in the muscle tissue of the auricula sinistra opposite the entry. The cage structure 10 will be in contact with the walls and the proximal end with retaining ring 4 is located in the entry region.

The connecting webs 2 joining the retaining ring 4 to cage structure 10 and its web elements extend in a curvilinear fashion in such a manner that initially they extend in proximal direction and subsequently are bent over distally in a semicircular form towards cage 10. Webs 2 are provided with perforations 6 which serve to secure a covering as shown in FIG. 1.

Implants proposed by the invention are connected to a guide catheter via the retaining ring 4 and a customary coupling mechanism, said catheter being under control of the attending physician through a catheter. These techniques are generally known and nave been described many times. It is also understood that retaining ring 4 may be suitably closed off to prevent thrombi from being flushed out, for example by tight-fitting elements, struts formed out of the retaining ring or by the coupling mechanism inserted into the retaining ring, may be in the form of a plate or ball interacting with a pincer-shaped holding element of the guide catheter or guide wire.

FIG. 3 is a photographic representation of the implant depicted in FIG. 2 shown from the proximal side. Via eight connecting webs 2 the retaining ring 4 is attached to the cage which is composed of cage webs 3. Each connecting web 2 branches into two webs 3 which make up the actual cage in the form of a meshwork. The mesh structure of the cage constitutes the periphery discernible in FIG. 3 which distally terminates in the rim formed by tips 5.

In the connecting webs 2 a plurality of perforations 6 are arranged which serve for a covering of the implant to be attached, in the example shown, by sewing. Such a cover may, for example, consist of Teflon film or coat. Moreover, the covering may also be attached to the implant structure without difficulty by adhesive methods, by spreading or immersing or an electrospinning process.

Anchor elements 7a are centrally extending from the retaining ring 4 and terminate in a tip 8. Barbs 9 are arranged on tip 8 and in the example shown point to the periphery of the cage. In the left anchor element the section can be seen out of which barb 9 has been cut.

FIG. 4 shows another variant of an inventive implant in accordance with alternative (a) which provides for anchor elements 7 with tip 8 and barb 9 to be arranged on tips 5 of the rim structure of the implant. An anchor element need not be attached to every tip; preferably two or four anchor elements spaced at regular intervals are provided.

Within the meaning of the present description the term "proximal" denotes the side or end of the implant facing the attending physician and catheter whereas the term "distal" is meant to identify the implant side facing away from the attending physician and pointing towards the rear wall of the auricula sinistra.

FIG. 5 shows an inventive implant as per alternative (b). The implant 1 is provided with connecting webs 2 originating from the retaining ring 4, wherein said connecting webs branch into webs 3 forming cage 10 proper. Webs 3 are linked with each other and terminate in tips 5 which are rounded so as not to cause traumatic effects.

Valiant (b) provides for the anchor elements 7b to originate from the retaining ring 4 between the connecting webs 2 and extend laterally towards the outside thus going beyond the outskirts of cage 10. The anchor elements 7b have a curved configuration, i.e. their curvature points in proximal direction. In this way, a cage is created that acts in opposite direction with respect to cage 10. Said anchor elements thus forming a circle of several arms abutting against the inner wall of the auricula sinistra and in this manner holding the implant in position.

FIG. 6 shows another photographic representation of the implant according to FIG. 5, which in this case is connected with a guidewire 13 that can be released by twisting after the implantation has been completed. Clearly visible is the cage structure formed by connecting webs 2 and webs 3, said structure terminating in tips 5 distally to the guidewire 13. Same as the connecting webs 2 the anchor elements 7b extend from the retaining ring 4, are arranged between neighboring connecting webs 2 and are of curved configuration such that they protrude beyond cage 10 towards the outside. Due to the curvature of the anchor elements 7b their end portions are capable of extending and acting outwardly as well as reversely (proximally) resulting in a barrier effect to be created that enables the implant to be securely retained at the placement site within the auricula sinistra.

Viewed from the proximal end, FIG. 7 depicts another variant of the implant 1 proposed by the invention. Extending from the retaining ring 4 webs 2 and 3 form the cage 10 (not separately referred to here). The anchor elements 7b originate from a retaining tube 14 which at its proximal end is mounted in and attached to the retaining ring 4. At the distal end of the retaining tube 14 the anchor elements 7b are arranged, of which two neighboring elements each are joined to form a loop terminating in a rounded tip 15. The tip of the anchor elements 7b has been inwardly bent, i.e. bent so as to point towards the cage. Anchor element 7b is intended to peripherally secure or brace itself with its outer side within the auricula sinistra. On the one hand, the inwardly curved tip 15 of the loop formed by two elements 7b prevents the tissue from suffering injuries and on the other causes anchor elements 7b to be tensioned which is conducive to and enhances the anchoring of the implant.

FIG. 8 is a representation of the implant according to FIG. 7 viewed from the side. The figure shows the retaining tube 14 mounted and fitted with its proximal end into the retaining ring 4. The retaining ring 4 is the starting point of the cage structure 10 formed by webs 2 and 3, with the webs 3 converging to term tips 5.

The anchor elements 7b spread out distally from retaining tube 14 and extend laterally beyond the cage structure towards the proximal end of the implant 1, wherein the ends of the anchor elements 7b are reversely bent pointing towards the cage. Two adjacent anchor elements 7b each form a loop converging into a tip 16 pointing in the direction of the cage. The anchor elements 7b brace themselves peripherally against the wall of the auricula sinistra and in this way make sure the implant is secured at the placement site.

The invention claimed is:

1. Medical implant (1) for the occlusion of a patient's auricula sinistra by endovascular means, said implant having a cage structure (10) comprising a plurality of webs (3) that are proximally attached to a retaining ring (4) via connecting webs (2) and distally limited by a rim of converging webs (3), wherein said implant (1) consists of a self-expanding material, has in contracted state the shape of a slotted tube and, after expansion, assumes the cage structure (10) of a diameter larger than that of the retaining ring (4) characterized in that at least one or several anchor elements (7b) are arranged distally to the cage structure (10), said anchor elements being proximally connected via a retaining tube (14) with the retaining ring (4), wherein the one or more anchor elements (7b) project laterally beyond the cage structure (10), extend in proximal direction in a curved configuration with the intention to be laterally supported against the muscle tissue of the auricula sinistra.

2. Implant according to claim 1, characterized by at least two anchor elements (7a, 7b) equally spaced over the circumference of the retaining ring (4).

3. Implant according to claim 2, characterized in that the barbs (9) of the anchor elements (7a) point outwardly.

4. Implant according to claim 1, characterized in that the connecting webs (2) extending from retaining ring (4) towards the cage structure (10) are provided with perforations (6).

5. Implant according to claim 1, characterized by a cover arranged in the proximal region.

6. Implant according to claim 5, characterized in that the cover consists of a Teflon film or coat.

7. Implant according to claim 5, characterized in that the cover is attached to the cage structure (10) by sewing making use of the perforations.

8. Implant according to claim 1, characterized in that the cage structure (10) is composed of a meshwork of branching and converging webs (3).

9. Implant according to claim 1, characterized in that the distal rim of the cage structure (10) has rounded tips (5).

10. Implant according to claim 1, characterized by a coupling for a guide catheter on the retaining ring (4).

11. Implant according to claim 1, characterized in that the cage structure (10) is provided in the proximal area with a central deepening portion in which the retaining ring (4) is arranged.

12. Implant according to claim 1, characterized in that the anchor elements (7b) are each arranged between two connecting webs (2) on the retaining ring (4).

13. Implant according to claim 1, characterized in that the anchor elements (7b) are provided with rounded ends (12).

14. Implant according to claim 1, characterized in that neighboring anchor elements (7b) are connected with each other in pairs.

15. Implant according to claim 12, characterized in that the tips of the anchor elements (7b) are bent inwardly pointing towards the cage structure (10).

16. Implant according to claim 1, characterized in that retaining ring (4), cage structure (10), and anchor elements (7a, 7b) consist of a shape-memory metal.

17. Implant according to claim 12, characterized in that the shape-memory metal is a nickel-titanium alloy.

18. Implant according to claim 12, characterized in that the implant is manufactured from a tube by laser cutting and its expanded shape is brought about by adopting a thermal forming method.

* * * * *